(12) United States Patent
Haser et al.

(10) Patent No.: US 6,468,059 B2
(45) Date of Patent: Oct. 22, 2002

(54) HOSE CASSETTE FOR A PERISTALTIC PUMP

(75) Inventors: Christian Haser, Stahnsdorf; Peter Zentner, Berlin; Gotthilf Mehner, Sulzbach, all of (DE)

(73) Assignee: W.O.M. World of Medicine GmbH (DE)

( * ) Notice: Subject to any disclaimer, the term of this patent is extended or adjusted under 35 U.S.C. 154(b) by 0 days.

(21) Appl. No.: 09/737,013

(22) Filed: Dec. 14, 2000

(65) Prior Publication Data

US 2001/0004444 A1 Jun. 21, 2001

(30) Foreign Application Priority Data

Dec. 15, 1999 (DE) .......................... 199 60 668

(51) Int. Cl.⁷ ........................... F04B 43/12; F04B 45/08
(52) U.S. Cl. ................. 417/477.1; 417/477.2; 417/477.3
(58) Field of Search .................. 417/477.1, 477.2, 417/477.3, 477.12, 476; 81/142, 148, 355, 407

(56) References Cited

U.S. PATENT DOCUMENTS

| | | | | |
|---|---|---|---|---|
| 3,137,240 A | * | 6/1964 | Hunt | 103/149 |
| 3,927,955 A | * | 12/1975 | Spinosa et al. | 417/477 |
| 4,187,057 A | * | 2/1980 | Xanthopoulos | 417/63 |
| 4,798,580 A | * | 1/1989 | DeMeo et al. | 604/30 |
| 5,131,823 A | * | 7/1992 | Guignard | 417/477 |
| 5,350,284 A | * | 9/1994 | Wehling | 417/474 |
| 5,433,588 A | * | 7/1995 | Monk et al. | 417/477.2 |
| 5,533,877 A | * | 7/1996 | Friedmann et al. | 417/477.1 |
| 5,568,912 A | * | 10/1996 | Minami et al. | 251/205 |
| 5,741,125 A | * | 4/1998 | Neftel et al. | 417/477.7 |
| 5,915,932 A | * | 6/1999 | Nabity et al. | 417/477.1 |

* cited by examiner

Primary Examiner—Charles G. Freay
Assistant Examiner—Han Lieh Liu
(74) Attorney, Agent, or Firm—McGlew and Tuttle, P.C.

(57) ABSTRACT

A hose cassette (1), for a peristaltic pump (2), includes a cassette housing (3) and a flexible hose (4) extending through cassette housing (3). The hose (4) is guided in the cassette housing (3) along a circular segment. The cassette housing (3) has a cutout (5) for the engagement of a roller wheel (6) of a peristaltic to pump (2) into the interior of said circular segment. The hose cassette has connection elements (7), (8) for connecting the cassette housing (3) to the peristaltic pump (2). At least one hose leg (9), (10) to be connected to the circular segment is displaceably held between a mounting position and an operating position in the cassette housing (3).

20 Claims, 4 Drawing Sheets

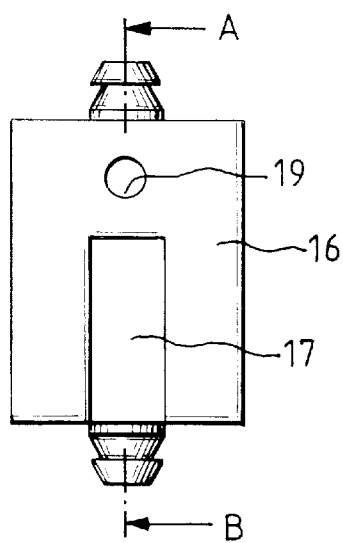
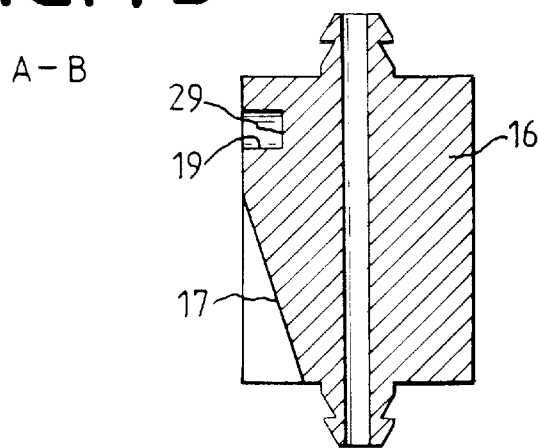
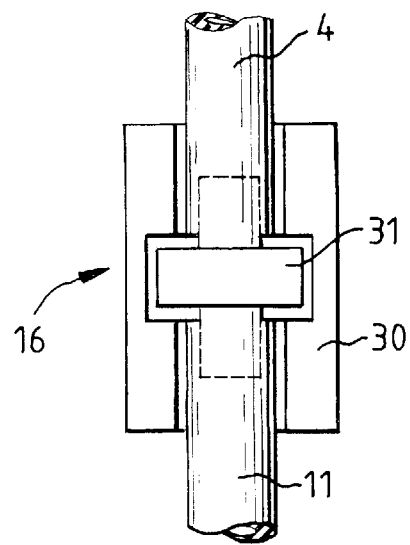

HOSE CASSETTE FOR A PERISTALTIC PUMP

FIELD OF THE INVENTION

The invention relates to a hose cassette for a peristaltic pump, comprising a cassette housing, a flexible hose extending through the cassette housing, the hose being guided in the cassette housing along a circular segment and the cassette housing having a cutout for the engagement of a roller wheel of the peristaltic pump into the interior of the circular segment, arid comprising connection elements for connecting the cassette housing to the peristaltic pump. The invention further relates to a peristaltic pump comprising such a cassette. Hose cassettes of the type mentioned above are in particular used as sucking and rinsing pumps for medical applications. Insofar the hose may perform the function of a rinsing or a sucking line. Examples for medical applications are the arthroscopy, the hyteroscopy and the cystoscopy. For medical applications, particularly sterility satisfying all requirements, is important, and therefore the hose is normally disposed of after an application, so to avoid cross contamination between different patients. The hose cassettes have thus to be economic to make, on one hand, and to permit simple handling, on the other hand.

BACKGROUND OF THE INVENTION

As to prior art peristaltic pumps, there are in principle two different basic configurations. The first basic con figuration consists in that the hose disposed around the roller wheel is pressed against the roller wheel by means of a pressure bracket or the like. Such embodiments are for example known from documents U.S. Pat. No. 4,798,580 and U.S. Pat. No. 5,044,902. Of a substantially similar mode of operation is the subject matter of document U.S. Pat. No. 4,798,580, according to which a cassette with a pressure bracket is provided behind the hose. The cassette is fixed by a lever closure mechanism, and simultaneously the hose is pressed by the pressure bracket against the roller wheel at the pump housing. In the subject matter of document U.S. Pat. No. 5,044,902, the roller wheel is integrated in the cassette, and when mounting in the cassette, the hose is pressed towards the cassette wall and against the latter by centering the roller wheel on its guiding portion.

The second basic configuration, on which the invention in principle relies, consists in that the hose is pulled with sufficient enclosing angle around the roller wheel by a tensional force of suitable size. Hereby a pressure bracket or the like will not be needed. The tensional force has to be adjusted, according to the elastic properties of the hose, such that in the area of a roller of the roller wheel, the inner cross section of the hose is reduced to virtually zero. Examples can be found in documents U.S. Pat. No. 4,537,561 and U.S. Pat. No. 5,213,483. In the insofar prior art embodiments, the hose is fixed at opposite ends of the cassette and extends in a straight line between such ends. The cassette is then pressed on in a radial direction, in relation to the roller wheel, towards the roller wheel and is fixed with suitable fixing elements. Hereby, by dimensioning the geometry of the cassette and of the connection elements according to the elasticity of the hose, a tensional force on the hose portion interacting with the roller wheel and meeting the requirements will be achieved; handling is however relatively complicated, and it is regularly necessary to use both, hands for putting the cassette in place. This is also caused by that the forces required to press the cassette on may be rather substantial, and some finesse will be required for precise positioning by manual operation against these forces.

SUMMARY OF THE INVENTION

In contrast thereto, the invention is based on the technical object to provide a hose cassette and a peristaltic pump permitting connection of the cassette to a pump housing in a particularly simple and handy manner.

For solving this object the invention teaches that at least one hose leg to be connected to the circular segment is displaceably held between a mounting position and an operating position in the cassette housing. Displaceability may be provided in a straight line or along a curve. The basic concept of the invention consists in that in a first mounting step, the cassette with the hose leg being in the mounting position is put in place at a pump housing, and in a second mounting step, by pulling at the displaceable hose leg, the hose will rest against the roller wheel with the required pressure. This is then the operating position of the hose leg. Hereby it is achieved that the hose cassette can in a simple way be mounted at a pump housing, and that without counter pressure from elastic forces of the hose. The cassette can thus easily be mounted with one hand. Immediately thereafter the required pressure of the hose around the roller wheel with sufficient tensional force is adjusted by a simple pull at the displaceable hose leg. It is understood that the displaceable hose leg is fixable in a suitable manner in the operating position, for example by latching. For this, too, one hand only is required, since the weight of the peristaltic pump generates sufficient counter force against the elastic forces of the hose.

It is preferred to adjust the operating position by that, when the cassette is mounted at the peristaltic pump, the displaceable hose leg is adjustable by pulling at the hose portion immediately following the displaceable hose leg and being disposed outside the cassette, the displaceable hose leg latching in the operating position. Basically, both hose legs may be held in a displaceable manner. In conjunction with other functions possibly to provide, it is however recommended that only one hose leg is displace able between the mounting position and the operating position, and that the other hose leg is fixed in the longitudinal direction of the hose.

In principle, the enclosing angle of the hose around the roller wheel is arbitrary, as long as a sufficient crosssection reduction will result with corresponding tensional force on the hose in the area of a roller. It is preferred that the circular segment and thus the enclosing angle of the hose around the roller wheel will extend over at least 90°, preferably 170° to 190°, most preferably 180°. It is suitable to form the hose at least in the area of the circular segment from a rubber-elastic material, in particular a natural or synthetic elastomer material, preferably a silicone caoutchouc or an elastomer polyurethane(co)polymer. The higher the modulus of elasticity, the lower the necessary tensional force at the displaceable hose leg.

In the embodiment with only one displaceable hose leg it is preferred that the fixed hose leg comprises a connection element having stop surfaces preferably extending orthogonally to the longitudinal extension of the hose, said stop surfaces resting against fixing surfaces in the cassette housing. By interaction of the stop surfaces with the fixing surfaces, the connection element and thus the hose leg are fixed virtually without any clearance. This embodiment permits that the connection element of the fixed hose leg comprises a pressure sensor communicating with the peristaltic pump, when the cassette is mounted at the peristaltic pump. The pressure sensor being in hydrostatic connection with a fluid flowing through the hose, may be adapted as a pressure transducer, the pressure acting on the sensor being transformed into an electrical value or an electrical signal, respectively. Communication with the peristaltic pump will then operate over complementary contacts at the pressure sensor and at the peristaltic pump. It is however also possible that the pressure sensor is adapted as a pressure membrane and is in mechanical connection with a pressure transducer provided in the peristaltic pump, when the hose cassette is mounted. This is particularly advantageous with regard to cost.

Preferably the displaceable hose leg is provided with a connection element comprising a latch element. In detail, the latch element may comprise a stop surface, by means of which for a cassette mounted at the peristaltic pump, a locking element provided at the peristaltic pump can be lifted, during the displacement of the displaceable hose leg, from the mounting position into the operating position against spring pressure from a locking position, and the latch element comprises adjacent to the stop surface a blocking surface in the direction of the operating position, the locking element engaging in its locking position behind said blocking surface. The particular advantage of this specific embodiment is that due to the arrangement of the blocking surface on one hand in the frame of the cassette and of the locking element on the other hand in the frame of the peristaltic pump, no special unlocking mechanism or no special unlocking handling is necessary when the cassette is removed from the pump housing. When, the cassette is removed from the pump housing, the locking element will come free from the blocking surface, with the consequence of release of the connection element and thus the relaxing of the hose by displacement of the displaceable hose leg into the mounting position. In the simplest case, the locking element is a locking pin.

Preferably the hose, possibly together with the connection elements, can be removed from the cassette housing. In detail: the cassette housing may have a substantially half-oval shape with two plane half-oval surfaces, one half-oval surface being closed and the opposite half-oval surface being open and comprising a cutout for engagement of the roller wheel. Through the open half-oval surface, the hose may be removed, if necessary together with its connection elements. Such an embodiment permits re-use of the cassette housing and thus a considerable reduction of waste. A rejected cassette is collected as waste and for instance returned to the manufacturer, who will then remove in a simple way the hose and the connection elements from the cassette, scrap those and take the cassette for renewed use.

The connection of the hose cassette to the peristaltic pump can be achieved in various ways. In any case it is a releasable connection. A preferred embodiment is characterized in that at least one form fit cutout is provided at a wall being orthogonal to the half-oval surfaces, and that spaced to the form fit cutout, in relation to the wall, at least one friction-drive element is provided, by means of said friction-drive element a releasable connection to the peristaltic pump being achieved by moving the friction-drive element in a direction being parallel to wall In this embodiment, application is as follows. An operator takes the cassette housing and puts it inclinedly in place at the peristaltic pump, thus establishing a form fit connection. After establishment of the form fit connection, the cassette in pressed in a tilting manner (axis of rotation at the form fit connection) to wards the peristaltic pump, thus the friction-drive connection being established, and the cassette is held safely in position at the pump housing.

The invention further relates to a peristaltic pump comprising a pump housing, a roller wheel projecting over the outside wall of the pump housing, and comprising a hose cassette according to the invention, wherein the connection elements being complementary to the connection elements of the cassette are provided at the outside wall. It is understood, herein, that the axis of rotation of the roller wheel is orthogonal to the outside wall and substantially coaxial with the circular segment. In a peristaltic pump according to the invention, various other functions may be covered by the hose cassette. The arrangement of a pressure transducer interacting with a pressure membrane, when the cassette is put in place, has been described above. Further it is possible that a drive motor of the roller wheel is controlled such that drive is only possible with mounted cassette. This can for instance be achieved by a switch or the like operated by the cassette put in place at the pump housing. A particularly advantageous embodiment is characterized in that for controlling the drive motor, a switching element is operable by the locking element. The switching element is activated in the locking position of the locking element, not however in a rest position obtained without mounted cassette. As a result, the roller wheel may only be controlled or rotationally driven, if (cumulatively) the cassette is mounted at the pump housing, and the displaceable hose leg is in the operating position.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 4a is a top view of a connection element for a displaceable hose leg;

FIG. 4b is a cross sectional view of a connection element for a displaceable hose leg;

FIG. 5 is an alternative embodiment to the subject matter of FIG. 4.

DESCRIPTION OF THE PREFERRED EMBODIMENT

Figure 1:
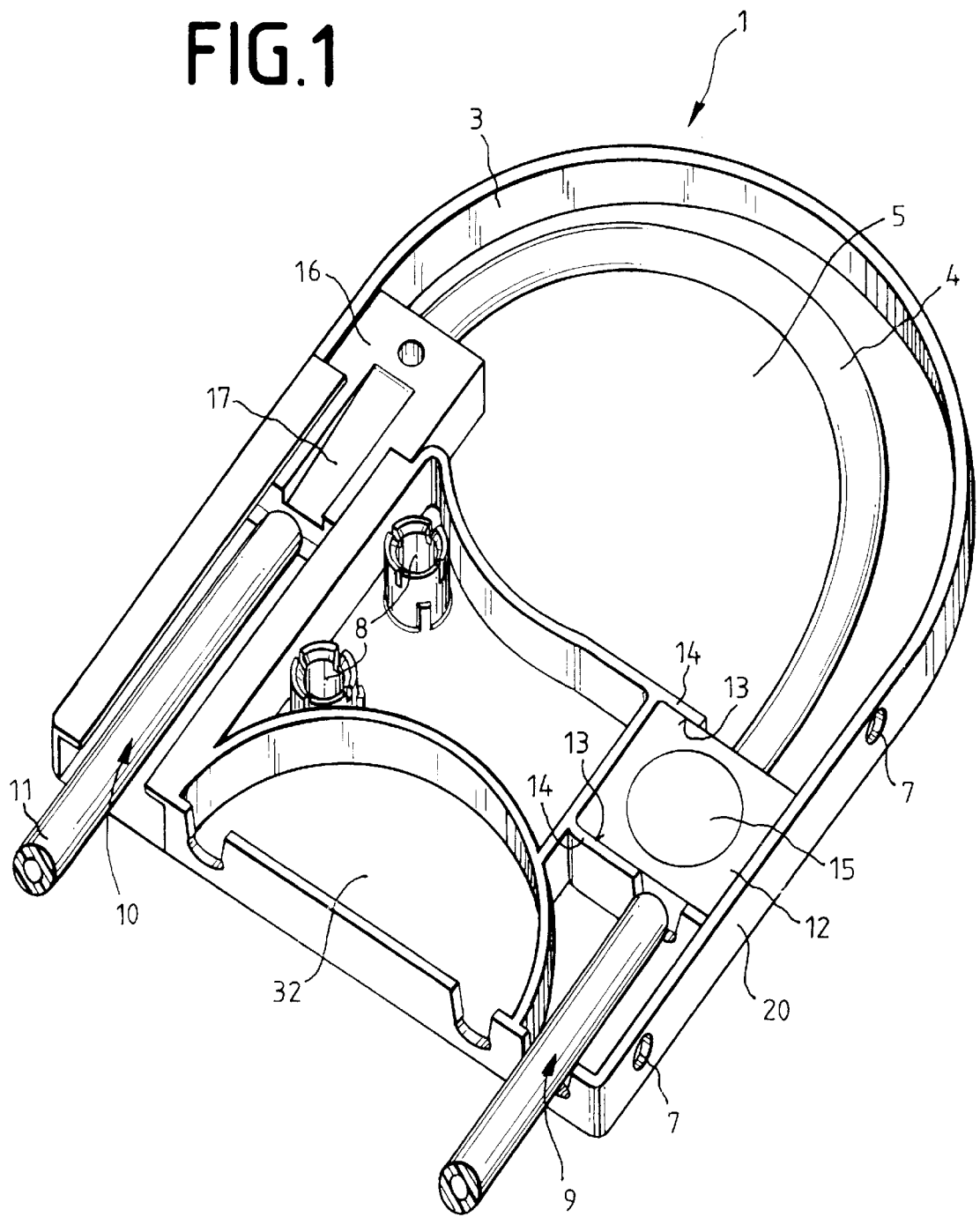
FIG. 1 is a total perspective view of a hose cassette according to the invention.
Figure 2:
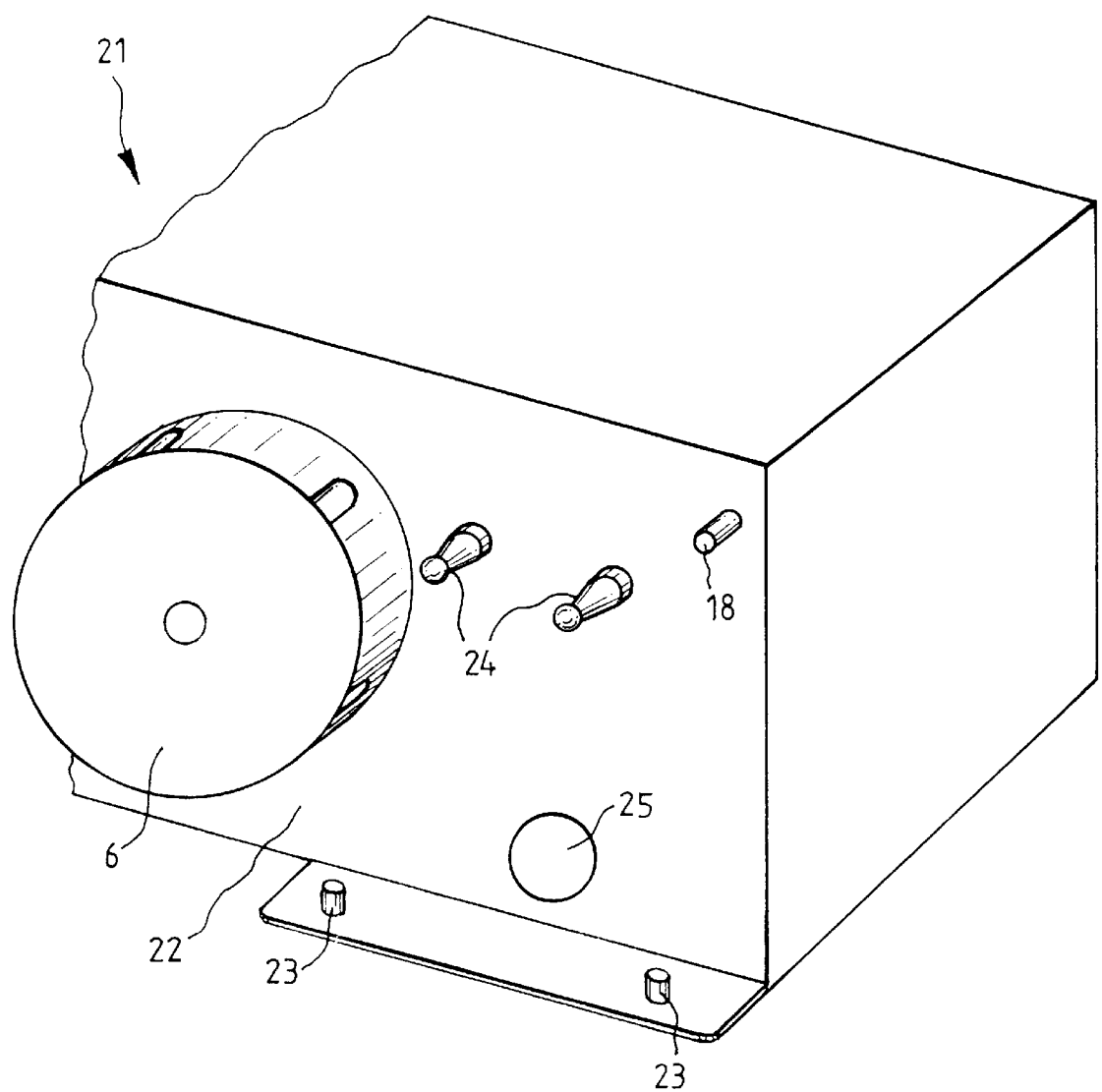
FIG. 2 is a perspective view of a peristaltic pump according to the invention.

Referring to the drawings in particular, FIG. 1 shows a hose cassette 1 for a peristaltic pump 2 (see also FIG. 2) with a cassette housing 3, a flexible hose 4 extending through cassette housing 3 and being guided in cassette housing 3 along a circular segment, in the example shown approx. 180°. Cassette housing 3 has a substantially half-oval shape with two plane half-oval surfaces, one half-oval surface being closed and the opposite half-oval surface being open and thus comprising a cutout 5 for engagement of roller wheel 6. Roller wheel 6 of peristaltic pump 2 engages with mounted hose cassette 1 into the interior of the circular segment. Further can be seen in FIG. 1 connection elements 7, 8 for the connection of cassette housing 3 to peristaltic pump 2. FIG. 2 shows that outside wall 22 of pump housing 21 carrying the roller wheel comprises connection elements 23, 34 being complementary to connection elements 7, 8 of the cassette. In FIG. 2 there can further be seen that roller wheel 6 projects over outside wall 22 of the pump housing. With mounted hose cassette 1, the axis of rotation is substantially coaxial with the circular segment of the guiding mechanism of hose 4 in cassette housing 3, as a comparison of FIGS. 1 and 2 will show.

Figure 3A:
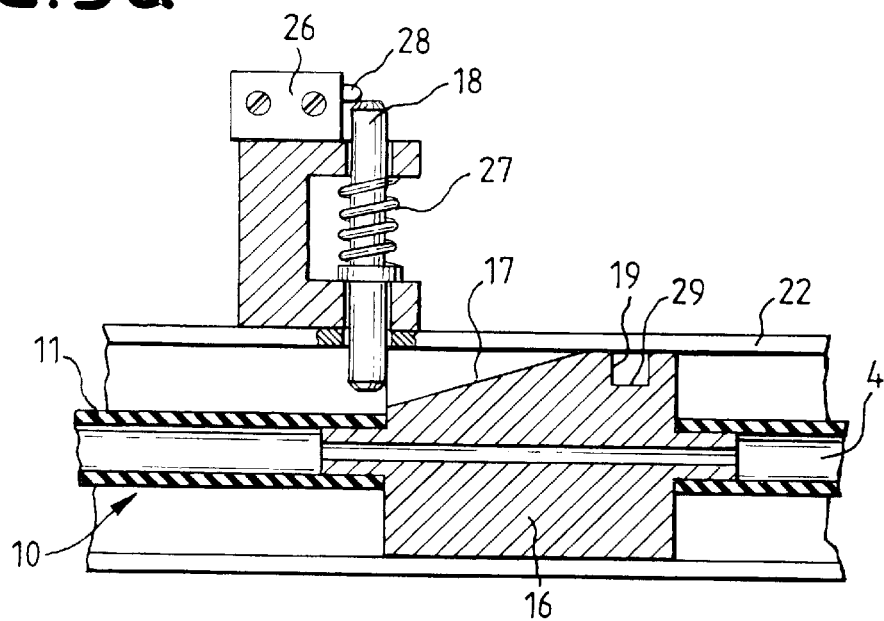
FIG. 3a is a cross sectional view showing a detail view in the area of a displaceable hose leg for a cassette mounted at the peristaltic pump, in a mounting position of the hose leg.
Figure 3B:
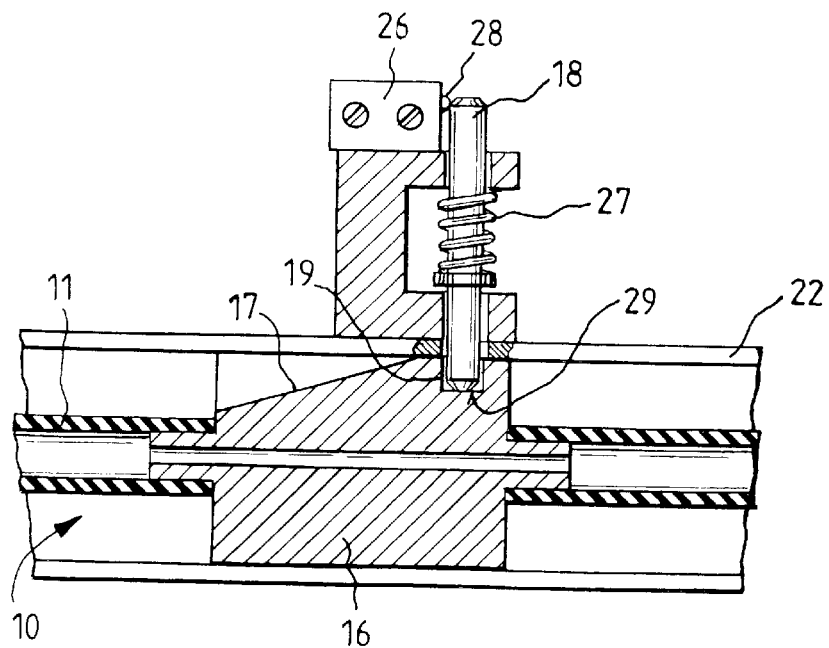
FIG. 3b is a cross sectional view showing a detail view in the area of a displaceable hose leg for a cassette mounted at the peristaltic pump, in an operating position of the hose leg.

From FIG. 1 can be taken that a hose leg 10 connected to the circular segment is placeably supported between a mounting position and an operating position. The mounting position and the operating position can in detail be seen in FIGS. 3a and 3b. In particular, a connection element 16 with a latch element is provided in the frame of the displaceable hose leg 10 forming a hose deployment means. The latch element comprises a stop surface 17, by means of which, for a cassette 1 mounted at peristaltic pump 2, a locking pin 18 is lifted against spring pressure from a rest position during the displacement of displaceable hose leg 10 from the mounting position into the operating position. The latch element comprises in the direction of the operating position adjacent to stop surface 17 a blocking surface 19, behind which, the locking element 18 will engage in its locking position. Further comparing FIGS. 3a and 3b, it will be seen that a switching element 26 is provided in the frame of peristaltic pump 2, said switching element interacting with locking pin 18. In FIG. 3a, locking pin 18 has been moved in its rest position beyond its locking position from outside wall 22 of pump housing 21, under the action of the force of compression spring 27. By suitable arrangement of the switching element 26, an operating element 28 of switching element 26 is accessible. During displacement of connection element 16 from the representation in FIG. 3a into the representation of FIG. 3b, locking pin 18 is displaced against the spring force of compression spring 27 in the direction within outside wall 22 of pump housing 21 by the action of stop surface 17. During this movement, operating element 28 of switching element 26 is operated.

As soon as the operating position (FIG. 3b) is achieved, locking pin 18 will fall into a cutout with a blocking surface 19 and thus into its locking position. Thereby hose 4 is held in the operating position against its internal elastic forces. It is important in this context that locking pin 18 will additionally hit on ground 29 of the cutout, the arrangement of switching element 26, the length of locking pin 18 and the arrangement of ground 29 being selected such that operating element 28 will remain actuated in the locking position of locking pin 18. As a result, by switching element 26, roller wheel 6 is only possible in the operating position of hose leg 10.

In FIGS. 4a and 4b there is shown in detail connection element 16 of displaceable hose leg 10 in two different orthogonal views. Again stop surface 17, blocking surface 19 and ground 29 can be seen. In this embodiment, connection element 16 is configured as one piece. However, a two or three-piece embodiment is also possible, as shown for example in FIG. 5 In the subject matter of FIG. 5, a connector 31 is fixably positioned in the direction of the longitudinal extension of hose 4 in a connection piece housing 30. Compared to the top view of FIG. 5, the connection piece housing 30 has a structure corresponding to the representation of FIG. 4a.

From FIG. 1 can be seen that the second hose leg 9 is fixed in the longitudinal direction of hose 4. In the frame of fixed hose leg 9 is configured a connection element 12 having stop surfaces 13 extending orthogonally to the longitudinal extension of hose 4. Stop surfaces 13 run up against fixing surfaces 14 in cassette housing 2. In the frame of connection element 12 of fixed hose leg 9 is provided a pressure sensor 15 communicating with peristaltic pump 2, when cassette 1 is mounted at peristaltic pump 2. In the embodiment, pressure sensor 15 is adapted as a pressure membrane 15 of a pressure chamber, and at pump housing 21 is mounted a pressure transducer 25 such that pressure membrane 15 rests against pressure transducer 25, when cassette 1 is mounted (see also FIG. 2). From FIG. 1 can be seen that hose 4 including connection elements 12, 16 can be removed from cassette housing 3. Removal is achieved in the direction approximately orthogonal towards top of the paper plane in the shown view.

Hose 4 consists in the area of the circular segment or between connection elements 12, 16 of a rubber-elastic material, namely silicone caoutchouc. Hose 4 may adjacent to connection elements 12, 16 be made from an identical or a different material. In particular, it is possible to use non-rubber-elastic materials, too.

Comparing FIGS. 1 and 2 the means for fixing hose cassette 1 to peristaltic pump 1 can be seen. In FIG. 1 is visible that at a wall 20 being orthogonal to the half-oval surfaces, two form fit cutouts 7 are provided, and that spaced to form fit cutouts 7, in relation to wall 20, two friction-drive connection elements 8 are provided. In the frame of the peristaltic pump, complementary connection elements 23, 24 are arranged. Connection elements 23 are holding pins 23 positively engaging into positive drive cutouts 7. Friction-drive connection elements 8 and complementary connection fittings 24 are adapted as a releasable friction-drive connection. For mounting hose cassette 1 at peristaltic pump 2, first form fit element cutouts 7 are positioned on holding pins 23 and are slid on, hose cassette 1 being held in a tilted manner with respect to outside wall 22. It is understood that between form fit cutouts 7 and holding pins 23 a sufficient clearance is provided. After mounting, hose cassette 1 is tilted against outside wall 22 and is pressed against, thus the connection between friction-drive connection elements 8 and connection fittings 24 being established, and hose cassette 1 being held at peristaltic pump 2, Removal is achieved in reversed sequence.

In the shown embodiment, hose 4 operates as a rinsing line. Irrespective of the shown embodiment, it is possible that a second hose is provided in the frame of the cassette, for instance operating as a discharge line, and shutter means may be provided in the frame of the peristaltic pump, such means blocking the second hose when the cassette is mounted. In the embodiment of FIG. 1, a cassette chamber 32 is provided for this purpose.

While specific embodiments of the invention have been shown and described in detail to illustrate the application of the principles of the invention, it will be understood that the invention may be embodied otherwise without departing from such principles.

What is claimed is:

1. A peristaltic pump hose cassette, comprising:
   a cassette housing with a circular segment and at least one pump connection surface for engagement with a peristaltic pump for connection to the peristaltic pump for use and for disconnection from the peristaltic pump for disposal;
   a flexible hose extending through said cassette housing, said flexible hose being guided in said cassette housing along said circular segment, said cassette housing having a cutout for the engagement of a roller wheel of a peristaltic pump into the interior of said circular segment;

tool-less connection elements connected to the cassette housing for connecting said cassette housing connection surface to the peristaltic pump and disconnecting said cassette housing connection surface from the peristaltic pump for disposal; and a displaceable hose leg portion connected to said flexible hose, said displaceable hose leg portion extending adjacent to said circular segment, said displaceable hose leg portion being moveable relative to said cassette housing and displacing said flexible hose to hold said flexible hose in one of a mounting position and an operating position in the cassette housing.

2. A hose cassette according to claim 1, further comprising another hose portion, wherein the operating position is adjustable for the cassette mounted at the peristaltic pump, said displaceable hose leg being adjustable by pulling at another hose portion immediately adjacent to and connected to said displaceable hose leg, said another hose portion being arranged outside of the cassette, said displaceable hose leg latching in said operating position.

3. A hose cassette according to claim 1, further comprising another hose portion connected to said displaceable hose leg, said flexible hose, said displaceable hose leg portion and said another portion form a hose leg that is displaceable between the mounting position and the operating position, said flexible hose having another hose leg that is fixed in longitudinal direction of an end portion of said flexible hose.

4. A hose cassette according to claim 1, wherein the circular element extends over at least 90°.

5. A hose cassette according to claim 1, wherein the circular element extends over at least 170° to 190°.

6. A hose cassette according to claim 1, wherein the circular element extends over substantially 180°.

7. A hose cassette according to claim 1, wherein said flexible hose is formed at least in an area of said circular segment from a rubber-elastic material.

8. A hose cassette according to claim 7, wherein said flexible hose is formed at least in an area of said circular segment from one or more of a natural elastomer material, synthetic elastomer material, a silicone caoutchouc and an elastomer polyurethane-(co)polymer.

9. A hose cassette according to claim 3, wherein said fixed hose leg comprises a connection element having stop surfaces extending orthogonally to a longitudinal extension of said flexible hose, said stop surfaces resting against fixing surfaces in said cassette housing.

10. A hose cassette according to claim 9, wherein said connection element of said fixed hose leg comprises a pressure sensor communicating with a peristaltic pump assembly, for the cassette when mounted at the peristaltic pump.

11. A hose cassette according to claim 1, wherein said displaceable hose leg comprises a connection element with a latch element.

12. A hose cassette according to claim 1, wherein the latch element has a stop surface for lifting a locking element of a cassette mounted at the peristaltic pump during the displacement of displaceable hose leg, from the mounting position into the operating position against a spring pressure from the locking position, and said latch element comprises adjacent to stop surface a blocking surface in the direction of the operating position, the locking element engaging in its locking position behind a blocking surface.

13. A hose cassette according to claim 12, wherein said locking element is configured as a locking pin.

14. A hose cassette according to claim 11, wherein said flexible hose together with said connection elements are removably mounted in said cassette housing.

15. A hose cassette according to claim 11, wherein said cassette housing has a substantially half-oval shape with two plane half-oval surfaces, one half-oval surface being closed and the opposite half-oval surface being open and comprising a cutout for engagement of a roller wheel of the peristaltic pump.

16. A hose cassette according to claim 15, further comprising a friction element, said cassette housing having at least one form fit cutout provided at a wall orthogonal to said half-oval surfaces, said form fit cutout being spaced from said half-oval surfaces, said friction element being releasably connected to a peristaltic pump by moving the friction element in a direction parallel to said wall.

17. A peristaltic pump and cassette combination comprising:

a pump housing;

a roller wheel projecting from an outside wall of said pump housing;

a hose cassette with a cassette housing with a circular segment and at least one pump interface surface for engagement with the peristaltic pump housing for connection to the peristaltic pump for use and for disconnection from the peristaltic pump for disposal, a flexible hose extending through said cassette housing, said flexible hose being guided in said cassette housing along a circular segment, said cassette housing having a cutout for the engagement of said roller wheel into the interior of said circular segment, cassette connection elements for connecting said cassette housing to the peristaltic pump and a displaceable hose leg portion of said flexible hose extending adjacent to said circular segment, said displaceable hose leg portion of said flexible hose being moveable relative to said cassette housing for displacement between a mounting position and an operating position in cassette housing; and connection elements provided at said outside wall of said pump housing, said connection elements being complementary to said cassette connection elements.

18. A peristaltic pump combination according to claim 17, further comprising a pressure sensor configured as a pressure chamber with a pressure membrane, and a pressure transducer, said pressure sensor being mounted at said pump housing such that with mounted cassette, said pressure membrane will rest against said pressure transducer.

19. A hose cassette according to claim 17, wherein said displaceable hose leg comprises a connection element with a latch element.

20. A peristaltic pump and cassette combination comprising:

a pump housing with an outside wall having a cassette interface region and connection elements provided at said outside wall of said pump housing;

a roller wheel projecting from an outside wall of said pump housing;

a hose cassette with a cassette housing with a circular segment and at least one pump interface surface that is complementary to said cassette interface region for engagement with the peristaltic pump housing for connection to the peristaltic pump for use and for disconnection from the peristaltic pump for disposal, a flexible hose extending through said cassette housing, said hose being guided in said cassette housing along a circular segment, said cassette housing having a cutout for the engagement of said roller wheel into the interior of said circular segment and cassette connection elements for connecting said cassette housing to the peristaltic pump, said pump housing connection elements being complementary to said cassette connection elements; and hose deployment means connected to said hose cassette and connected to said flexible hose extending through said cassette housing, said hose deployment means for moving said flexible hose relative to said cassette housing for displacement of said flexible hose between a mounting position in said cassette housing and an operating position in said cassette housing and for holding said flexible hose in one of said a mounting position in said cassette housing and said operating position in said cassette housing.

* * * * *